(12) United States Patent
Schieber et al.

(10) Patent No.: US 8,414,518 B2
(45) Date of Patent: Apr. 9, 2013

(54) GLAUCOMA TREATMENT METHOD

(75) Inventors: Andrew T. Schieber, Golden Valley, MN (US); Charles L. Euteneuer, St. Michael, MN (US)

(73) Assignee: Ivantis, Inc., Irvine, CA (US)

( * ) Notice: Subject to any disclaimer, the term of this patent is extended or adjusted under 35 U.S.C. 154(b) by 0 days.

(21) Appl. No.: 13/425,874

(22) Filed: Mar. 21, 2012

(65) Prior Publication Data
US 2012/0179087 A1    Jul. 12, 2012

Related U.S. Application Data

(60) Continuation of application No. 12/775,266, filed on May 6, 2010, now Pat. No. 8,282,592, which is a division of application No. 11/860,318, filed on Sep. 24, 2007, now Pat. No. 7,740,604.

(51) Int. Cl.
| | |
|---|---|
| *A61M 5/00* | (2006.01) |
| *A61M 25/00* | (2006.01) |
| *A61F 9/00* | (2006.01) |
| A61F 9/007 | (2006.01) |
| A61M 1/00 | (2006.01) |
| A61M 31/00 | (2006.01) |

(52) U.S. Cl. .................. 604/8; 604/9; 604/10; 623/4.1; 623/6.64

(58) Field of Classification Search .................. 604/8, 9, 604/10, 48, 500, 93.01; 623/1.1, 4.1, 6.64, 623/23.64
See application file for complete search history.

(56) References Cited

U.S. PATENT DOCUMENTS

| | | | |
|---|---|---|---|
| 3,788,327 | A | 1/1974 | Donowitz et al. |
| 3,948,271 | A | 4/1976 | Akiyama |
| 4,037,604 | A | 7/1977 | Newkirk |
| (Continued) | | | |

FOREIGN PATENT DOCUMENTS

| | | |
|---|---|---|
| AU | 1998/76197 B2 | 2/1999 |
| CN | 1950091 A | 4/2007 |
| (Continued) | | |

OTHER PUBLICATIONS

Lynch, Mary G.; U.S. Appl. No. 60/131,030 entitled "Devices and methods for treating glaucoma by enhancing aqueous outflow through schlemm's canal and anterior chamber angle," filed Apr. 26, 1999.

(Continued)

*Primary Examiner* — Leslie Deak
*Assistant Examiner* — Adam Marcetich
(74) *Attorney, Agent, or Firm* — Shay Glenn LLP

(57) ABSTRACT

An ocular implant adapted to reside at least partially in a portion of Schlemm's canal of an eye. In some embodiments the implant has a body extending in a curved volume whose longitudinal axis forms an arc of a circle, and a plurality of open areas and strut areas formed in the body, the open areas extending over more than 50% of a surface defining the curved volume, the strut areas surrounding the open areas, the body having a diameter of between 0.005 inches and 0.04 inches. The invention also provides a method of treating glaucoma including the steps of supporting tissue forming Schlemm's canal in an eye with an implant extending at least partially in the canal along an axial length within the canal; and contacting with the implant less than 50% of the tissue forming the canal along the axial length.

18 Claims, 19 Drawing Sheets

U.S. PATENT DOCUMENTS

| | | |
|---|---|---|
| 4,428,746 A | 1/1984 | Mendez |
| 4,457,757 A | 7/1984 | Molteno |
| 4,722,724 A | 2/1988 | Schocket |
| 4,733,665 A | 3/1988 | Palmaz |
| 4,750,901 A | 6/1988 | Molteno |
| 4,826,478 A | 5/1989 | Schocket |
| 4,886,488 A | 12/1989 | White |
| 4,936,825 A | 6/1990 | Ungerleider |
| 4,946,436 A | 8/1990 | Smith |
| 4,968,296 A | 11/1990 | Ritch et al. |
| 5,092,837 A | 3/1992 | Ritch et al. |
| 5,127,901 A | 7/1992 | Odrich |
| 5,178,604 A | 1/1993 | Baerveldt et al. |
| 5,180,362 A | 1/1993 | Worst |
| 5,213,569 A | 5/1993 | Davis |
| 5,246,452 A | 9/1993 | Sinnott |
| 5,360,399 A | 11/1994 | Stegmann |
| 5,372,577 A | 12/1994 | Ungerleider |
| 5,454,796 A | 10/1995 | Krupin |
| 5,458,615 A | 10/1995 | Klemm et al. |
| 5,591,223 A | 1/1997 | Lock et al. |
| 5,626,558 A | 5/1997 | Suson |
| 5,792,099 A | 8/1998 | DeCamp et al. |
| 5,807,302 A | 9/1998 | Wandel |
| 5,865,831 A | 2/1999 | Cozean et al. |
| 5,868,697 A | 2/1999 | Richter et al. |
| 5,879,319 A | 3/1999 | Pynson et al. |
| 5,893,837 A | 4/1999 | Eagles et al. |
| 5,968,058 A | 10/1999 | Richter et al. |
| 6,007,511 A | 12/1999 | Prywes |
| 6,050,970 A | 4/2000 | Baerveldt |
| 6,102,045 A | 8/2000 | Nordquist et al. |
| 6,186,974 B1 | 2/2001 | Allan et al. |
| 6,221,078 B1 | 4/2001 | Bylsma |
| 6,238,409 B1 | 5/2001 | Hojeibane |
| D444,874 S | 7/2001 | Haffner et al. |
| 6,375,642 B1 | 4/2002 | Grieshaber et al. |
| 6,450,984 B1 | 9/2002 | Lynch et al. |
| 6,464,724 B1 | 10/2002 | Lynch et al. |
| 6,471,666 B1 | 10/2002 | Odrich |
| 6,494,857 B1 | 12/2002 | Neuhann |
| 6,508,779 B1 | 1/2003 | Suson |
| 6,524,275 B1 | 2/2003 | Lynch et al. |
| 6,533,764 B1 | 3/2003 | Haffner et al. |
| 6,533,768 B1 | 3/2003 | Hill |
| 6,544,208 B2 | 4/2003 | Ethier et al. |
| 6,544,249 B1 | 4/2003 | Yu et al. |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,699,210 B2 | 3/2004 | Williams et al. |
| 6,699,211 B2 | 3/2004 | Savage |
| 6,726,676 B2 | 4/2004 | Stegmann et al. |
| D490,152 S | 5/2004 | Myall et al. |
| 6,730,056 B1 | 5/2004 | Ghaem et al. |
| 6,736,791 B1 | 5/2004 | Tu et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,881,198 B2 | 4/2005 | Brown |
| 6,939,298 B2 | 9/2005 | Brown et al. |
| 6,955,656 B2 | 10/2005 | Bergheim et al. |
| 6,962,573 B1 | 11/2005 | Wilcox |
| 6,981,958 B1 * | 1/2006 | Gharib et al. ............... 604/8 |
| 6,989,007 B2 | 1/2006 | Shadduck |
| 7,094,225 B2 | 8/2006 | Tu et al. |
| 7,135,009 B2 | 11/2006 | Tu et al. |
| 7,147,650 B2 | 12/2006 | Lee |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,207,965 B2 | 4/2007 | Simon |
| 7,207,980 B2 | 4/2007 | Christian et al. |
| 7,220,238 B2 | 5/2007 | Lynch et al. |
| 7,273,475 B2 | 9/2007 | Tu et al. |
| 7,297,130 B2 | 11/2007 | Bergheim et al. |
| 7,331,984 B2 | 2/2008 | Tu et al. |
| 7,740,604 B2 | 6/2010 | Schieber et al. |
| 8,012,115 B2 | 9/2011 | Karageozian |
| 2002/0003546 A1 | 1/2002 | Mochimaru et al. |
| 2002/0013546 A1 | 1/2002 | Grieshaber et al. |
| 2002/0013572 A1 | 1/2002 | Berlin |
| 2002/0072673 A1 | 6/2002 | Yamamoto et al. |
| 2002/0133168 A1 | 9/2002 | Smedley et al. |
| 2002/0143284 A1 | 10/2002 | Tu et al. |
| 2003/0055372 A1 | 3/2003 | Lynch et al. |
| 2003/0060748 A1 | 3/2003 | Baikoff |
| 2003/0060752 A1 | 3/2003 | Bergheim et al. |
| 2003/0093084 A1 | 5/2003 | Nissan et al. |
| 2003/0097151 A1 | 5/2003 | Smedley et al. |
| 2003/0181848 A1 | 9/2003 | Bergheim et al. |
| 2003/0187384 A1 | 10/2003 | Bergheim et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0024453 A1 | 2/2004 | Castillejos |
| 2004/0082939 A1 | 4/2004 | Berlin |
| 2004/0088048 A1 | 5/2004 | Richter et al. |
| 2004/0098124 A1 | 5/2004 | Freeman et al. |
| 2004/0102729 A1 | 5/2004 | Haffner et al. |
| 2004/0106975 A1 | 6/2004 | Solovay et al. |
| 2004/0111050 A1 | 6/2004 | Smedley et al. |
| 2004/0127843 A1 | 7/2004 | Tu et al. |
| 2004/0147870 A1 | 7/2004 | Burns et al. |
| 2004/0193095 A1 | 9/2004 | Shadduck |
| 2004/0193262 A1 * | 9/2004 | Shadduck ............... 623/4.1 |
| 2004/0210181 A1 * | 10/2004 | Vass et al. ............... 604/8 |
| 2004/0210185 A1 | 10/2004 | Tu et al. |
| 2004/0216749 A1 | 11/2004 | Tu |
| 2004/0225357 A1 | 11/2004 | Worst et al. |
| 2004/0249333 A1 | 12/2004 | Bergheim et al. |
| 2004/0254519 A1 | 12/2004 | Tu et al. |
| 2004/0254520 A1 | 12/2004 | Porteous et al. |
| 2004/0260228 A1 | 12/2004 | Lynch et al. |
| 2005/0049578 A1 | 3/2005 | Tu et al. |
| 2005/0090806 A1 | 4/2005 | Lynch et al. |
| 2005/0090807 A1 | 4/2005 | Lynch et al. |
| 2005/0107734 A1 | 5/2005 | Coroneo |
| 2005/0119601 A9 | 6/2005 | Lynch et al. |
| 2005/0119636 A1 | 6/2005 | Haffner et al. |
| 2005/0125003 A1 | 6/2005 | Pinchuk et al. |
| 2005/0154443 A1 | 7/2005 | Linder et al. |
| 2005/0165385 A1 | 7/2005 | Simon |
| 2005/0192527 A1 | 9/2005 | Gharib et al. |
| 2005/0197667 A1 | 9/2005 | Chan et al. |
| 2005/0203542 A1 | 9/2005 | Weber et al. |
| 2005/0209549 A1 | 9/2005 | Bergheim et al. |
| 2005/0209550 A1 | 9/2005 | Bergheim et al. |
| 2005/0244464 A1 | 11/2005 | Hughes |
| 2005/0250788 A1 | 11/2005 | Tu et al. |
| 2005/0260186 A1 | 11/2005 | Bookbinder et al. |
| 2005/0266047 A1 | 12/2005 | Tu et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0288619 A1 | 12/2005 | Gharib et al. |
| 2006/0032507 A1 | 2/2006 | Tu |
| 2006/0052879 A1 | 3/2006 | Kolb |
| 2006/0069340 A1 | 3/2006 | Simon |
| 2006/0074375 A1 | 4/2006 | Bergheim et al. |
| 2006/0079828 A1 | 4/2006 | Brown |
| 2006/0084907 A1 | 4/2006 | Bergheim et al. |
| 2006/0106370 A1 | 5/2006 | Baerveldt et al. |
| 2006/0116626 A1 | 6/2006 | Smedley et al. |
| 2006/0149194 A1 | 7/2006 | Conston et al. |
| 2006/0154981 A1 | 7/2006 | Klimko et al. |
| 2006/0155238 A1 | 7/2006 | Shields |
| 2006/0155300 A1 | 7/2006 | Stamper et al. |
| 2006/0173397 A1 | 8/2006 | Tu et al. |
| 2006/0189915 A1 | 8/2006 | Camras et al. |
| 2006/0189916 A1 | 8/2006 | Bas et al. |
| 2006/0189917 A1 | 8/2006 | Mayr et al. |
| 2006/0195055 A1 | 8/2006 | Bergheim et al. |
| 2006/0195056 A1 | 8/2006 | Bergheim et al. |
| 2006/0195187 A1 | 8/2006 | Stegmann et al. |

| | | | |
|---|---|---|---|
| 2006/0200113 A1 | 9/2006 | Haffner et al. | |
| 2006/0241749 A1 | 10/2006 | Tu et al. | |
| 2007/0010827 A1 | 1/2007 | Tu et al. | |
| 2007/0073275 A1 | 3/2007 | Conston et al. | |
| 2007/0088432 A1 | 4/2007 | Solovay et al. | |
| 2007/0106200 A1 | 5/2007 | Levy | |
| 2007/0106236 A1 | 5/2007 | Coroneo | |
| 2007/0112292 A1 | 5/2007 | Tu et al. | |
| 2007/0118147 A1 | 5/2007 | Smedley et al. | |
| 2007/0191863 A1 | 8/2007 | De Juan, Jr. et al. | |
| 2007/0270945 A1 | 11/2007 | Kobayashi et al. | |
| 2007/0276315 A1 | 11/2007 | Haffner et al. | |
| 2007/0276316 A1 | 11/2007 | Haffner et al. | |
| 2007/0282244 A1 | 12/2007 | Tu et al. | |
| 2007/0282245 A1 | 12/2007 | Tu et al. | |
| 2007/0293807 A1 | 12/2007 | Lynch et al. | |
| 2007/0298068 A1* | 12/2007 | Badawi et al. | 424/423 |
| 2008/0015488 A1 | 1/2008 | Tu et al. | |
| 2008/0045878 A1 | 2/2008 | Bergheim et al. | |
| 2008/0228127 A1 | 9/2008 | Burns et al. | |
| 2009/0030381 A1 | 1/2009 | Lind et al. | |
| 2009/0043321 A1 | 2/2009 | Conston et al. | |
| 2009/0069786 A1 | 3/2009 | Vesely et al. | |
| 2009/0082860 A1 | 3/2009 | Schieber et al. | |
| 2009/0082862 A1 | 3/2009 | Schieber et al. | |
| 2009/0104248 A1 | 4/2009 | Rapacki et al. | |
| 2009/0132040 A1 | 5/2009 | Frion et al. | |
| 2009/0182421 A1 | 7/2009 | Silvestrini et al. | |
| 2009/0227934 A1 | 9/2009 | Euteneuer et al. | |
| 2010/0121342 A1 | 5/2010 | Schieber et al. | |
| 2010/0137981 A1 | 6/2010 | Silvestrini et al. | |
| 2010/0222733 A1* | 9/2010 | Schieber et al. | 604/8 |
| 2011/0009874 A1 | 1/2011 | Wardle et al. | |
| 2011/0009958 A1 | 1/2011 | Wardle et al. | |
| 2011/0098809 A1 | 4/2011 | Wardle et al. | |
| 2011/0196487 A1 | 8/2011 | Badawi et al. | |
| 2011/0319806 A1 | 12/2011 | Wardle | |
| 2012/0136439 A1 | 5/2012 | Schieber et al. | |

FOREIGN PATENT DOCUMENTS

| | | | |
|---|---|---|---|
| DE | 19840047 A1 | 3/2000 | |
| WO | WO 00/07525 A1 | 2/2000 | |
| WO | WO 00/64389 A1 | 11/2000 | |
| WO | WO 00/64393 A1 | 11/2000 | |
| WO | WO 01/97727 A1 | 12/2001 | |
| WO | WO 02/36052 A1 | 5/2002 | |
| WO | WO 02/074052 A2 | 9/2002 | |
| WO | WO 02/080811 A2 | 10/2002 | |
| WO | WO 03/015659 A2 | 2/2003 | |
| WO | WO 03/045290 A1 | 6/2003 | |
| WO | WO 2004/093761 A1 | 11/2004 | |
| WO | WO 2005/105197 A2 | 11/2005 | |
| WO | WO 2006/066103 A2 | 6/2006 | |
| WO | WO 2008/002377 A1 | 1/2008 | |

OTHER PUBLICATIONS

Bahler, et al.; Trabecular bypass stents decrease intraocular pressure in cultured human anterior segments; Amer. Journal of Ophthalmology; vol. 138, No. 6; pp. 988-994.e2; Dec. 2004.

D'Ermo, et al.; Our results with the operation of ab externo trabeculotomy; Ophthalmologica; vol. 163; pp. 347-355; Feb. 1971.

Ellingsen et al.; Trabeculotomy and sinusotomy in enucleated human eyes; Investigative Ophthalmology; vol. 11; pp. 21-28; Jan. 1972.

Grant; Experimental aqueous perfusion in enucleated human eyes; Archives of Ophthalmology; vol. 69; pp. 783-801; Jun. 1963.

Johnstone et al.; "Microsurgery of Schlemm's Canal and the Human Aqueous Outflow System;" American Journal of Ophthalmology, vol. 76 (6): 906-917; Dec. 1973.

Lee et al.; Aqueous-venous shunt and intraocular pressure. Preliminary report of animal studies; Investigative Ophthalmology; vol. 5; No. 1; pp. 59-64; Feb. 1966.

Moses, Robert; The effect of intraocular pressure on resistance to outflow; Survey of Ophthalmology; vol. 22; No. 2; pp. 88-100; Sep.-Oct. 1977.

Mäepea et al.; The pressures in the episcleral veins, schlemm's canal and the trabecular meshwork in monkeys: effects of changes in intraocular pressure; Exp. Eye Res.; vol. 49; pp. 645-663; Oct. 1989.

Rosenquist et al.; Outflow resistance of enucleated human eyes at two different perfusion pressures and different extends of trabeculotomy; Current Eye Res.; vol. 8; No. 12; pp. 1233-1240; Dec. 1989.

Savage, James; Gonioscopy in the management of glaucoma; Am. Academy of Ophthalmology; Focal Points; vol. XXIV; No. 3; pp. 1-14; Mar. 2006.

Schultz, Jared; Canaloplasty procedure shows promise for open-angle glaucoma in European study; Ocular Surgery News; vol. 34; Mar. 1, 2007.

Smit et al.; Effects of viscoelastic injection into schlemm's canal in primate and human eyes; J. Am. Academy of Ophthalmology; vol. 109; No. 4; pp. 786-792; Apr. 20002.

Spiegel et al.; Schlemm's canal implant: a new method to lower intraocular pressure in patients with POAG?; Ophthalmic Surgery and Lasers; vol. 30; No. 6; pp. 492-494; Jun. 1999.

Wardle et al.; U.S. Appl. No. 13/160,355 entitled "Ocular implants for delivery into the eye," filed Jun. 14, 2011.

Wardle et al.; U.S. Appl. No. 13/330,592 entitled "Delivering Ocular Implants Into the Eye," filed Dec. 19, 2011.

\* cited by examiner

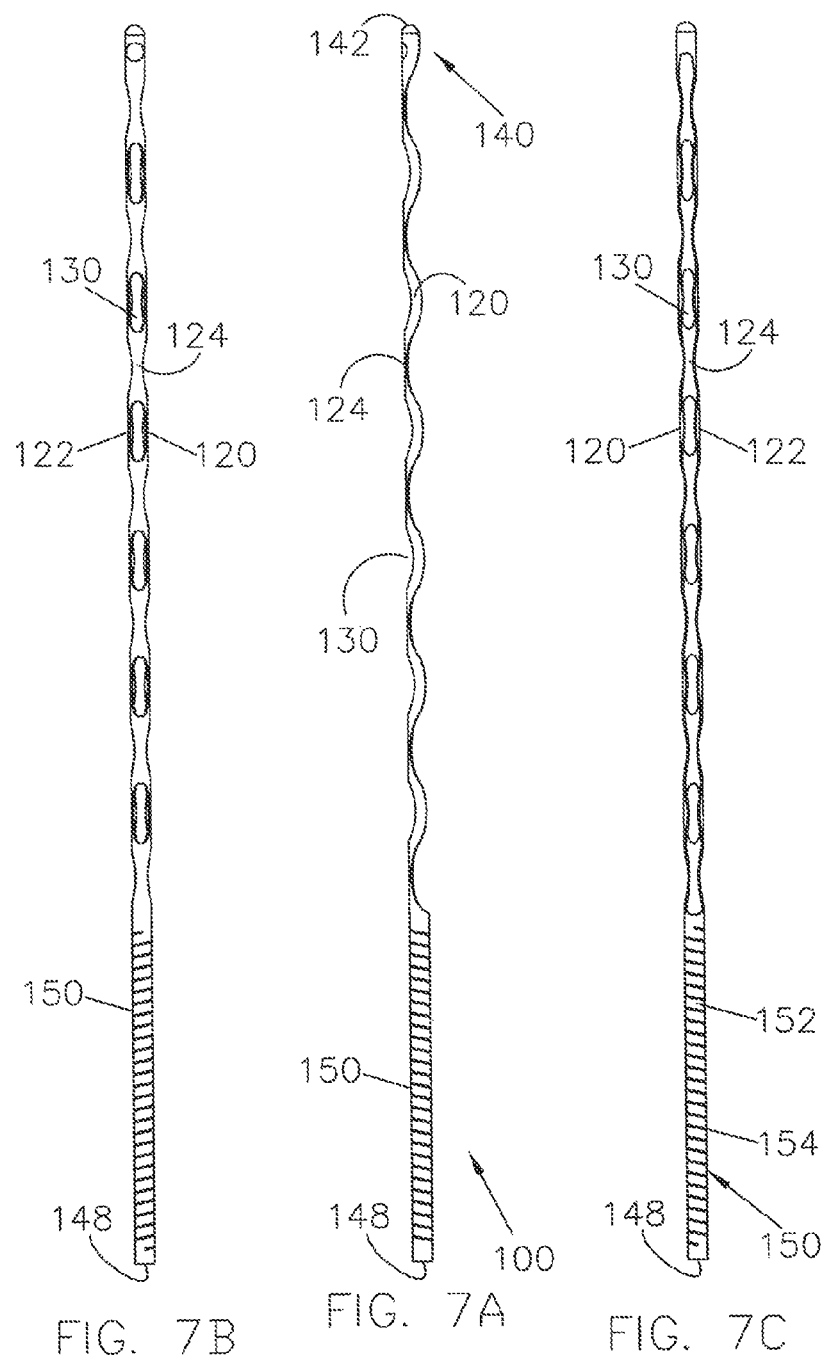

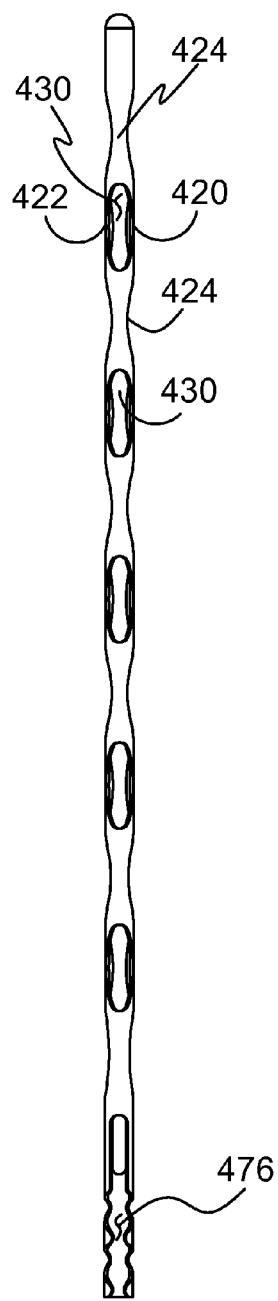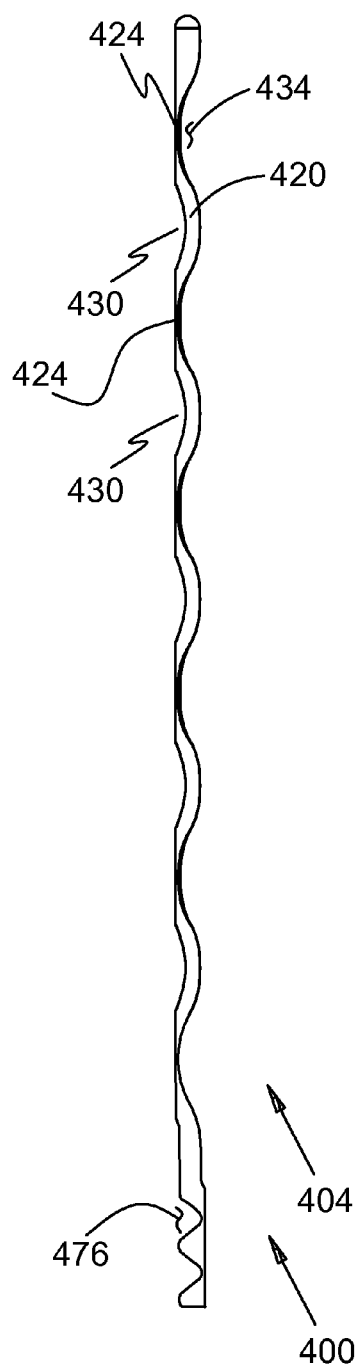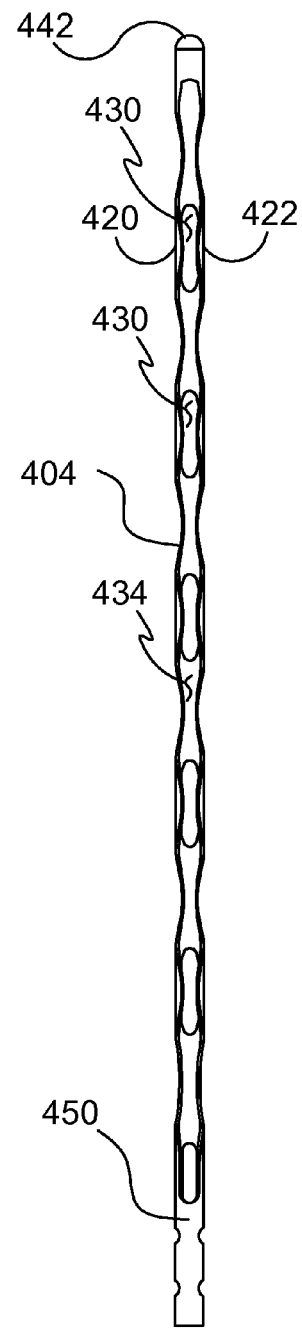
FIG. 13B
FIG. 13A
FIG. 13C

GLAUCOMA TREATMENT METHOD

CROSS-REFERENCE TO RELATED APPLICATIONS

This application is a continuation of U.S. application Ser. No. 12/775,266, filed May 6, 2010, now U.S. Pat. No. 8,282,592 entitled "Glaucoma Treatment Method", which application is a divisional of U.S. application Ser. No. 11/860,318, filed Sep. 24, 2007, now U.S. Pat. No. 7,740,604, entitled "Ocular Implants"; all of which are incorporated by reference herein.

FIELD OF THE INVENTION

The present invention relates generally to devices that are implanted within the eye. More particularly, the present invention relates to devices that facilitate the transfer of fluid from within one area of the eye to another area of the eye.

BACKGROUND OF THE INVENTION

According to a draft report by The National Eye Institute (NEI) at The United States National Institutes of Health (NIH), glaucoma is now the leading cause of irreversible blindness worldwide and the second leading cause of blindness, behind cataract, in the world. Thus, the NEI draft report concludes, "it is critical that significant emphasis and resources continue to be devoted to determining the pathophysiology and management of this disease." Glaucoma researchers have found a strong correlation between high intraocular pressure and glaucoma. For this reason, eye care professionals routinely screen patients for glaucoma by measuring intraocular pressure using a device known as a tonometer. Many modern tonometers make this measurement by blowing a sudden puff of air against the outer surface of the eye.

The eye can be conceptualized as a ball filled with fluid. There are two types of fluid inside the eye. The cavity behind the lens is filled with a viscous fluid known as vitreous humor. The cavities in front of the lens are filled with a fluid know as aqueous humor. Whenever a person views an object, he or she is viewing that object through both the vitreous humor and the aqueous humor.

Whenever a person views an object, he or she is also viewing that object through the cornea and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the anterior chamber of the eye through the trabecular meshwork and into Schlemm's canal as new aqueous humor is secreted by the epithelial cells of the ciliary body. This excess aqueous humor enters the venous blood stream from Schlemm's canal and is carried along with the venous blood leaving the eye.

When the natural drainage mechanisms of the eye stop functioning properly, the pressure inside the eye begins to rise. Researchers have theorized prolonged exposure to high intraocular pressure causes damage to the optic nerve that transmits sensory information from the eye to the brain. This damage to the optic nerve results in loss of peripheral vision. As glaucoma progresses, more and more of the visual field is lost until the patient is completely blind.

In addition to drug treatments, a variety of surgical treatments for glaucoma have been performed. For example, shunts were implanted to direct aqueous humor from the anterior chamber to the extraocular vein (Lee and Scheppens, "Aqueous-venous shunt and intraocular pressure," *Investigative Ophthalmology* (February 1966)). Other early glaucoma treatment implants led from the anterior chamber to a subconjunctival bleb (e.g., U.S. Pat. Nos. 4,968,296 and 5,180,362). Still others were shunts leading from the anterior chamber to a point just inside Schlemm's canal (Spiegel et al., "Schlemm's canal implant: a new method to lower intraocular pressure in patients with POAG?" *Ophthalmic Surgery and Lasers* (June 1999); U.S. Pat. Nos. 6,450,984; 6,450,984).

SUMMARY OF THE INVENTION

While some prior glaucoma treatment implants did provide a flow path between the anterior chamber and Schlemm's canal, these prior devices failed to recognize (1) the importance of supporting a significant portion of Schlemm's canal in a patent state or (2) the harm to adjacent tissue caused by relatively high fluid flow rates at or around any portion of the device. The ocular implant devices and methods of this invention address one or both of these design criteria.

According to one aspect of the invention, the ocular implant may be inserted into Schlemm's canal of an eye to facilitate the flow of aqueous humor out of the anterior chamber of the eye by, e.g., supporting tissue in the trabecular meshwork and in Schlemm's canal. The flow facilitated by the presence of the ocular implant may include axial flow along Schlemm's canal, flow into Schlemm's canal from the anterior chamber of the eye, and flow leaving Schlemm's canal via the outlets that communicate with the canal.

After exiting Schlemm's canal via the outlets, aqueous humor enters the venous blood stream and is carried along with the venous blood leaving the eye. The pressure of the venous system tends to be around 5-10 mmHg above atmospheric pressure. Accordingly, the venous system provides a pressure backstop which assures that the pressure in the anterior chamber of the eye remains above atmospheric pressure.

Some exemplary ocular implants disclosed in this document comprise a body having a plurality of open areas, strut areas and spine areas formed therein. The strut areas and spine areas act as reinforcing structures that hold the walls of Schlemm's canal in an patent state so that the walls of the canal provide a flow channel or fistula. Furthermore, the spine areas and the strut areas may be sized and shaped to reinforce Schlemm's canal while occupying a relatively small portion of the total lateral cross sectional area of Schlemm's canal. When this is the case, the ocular implant provides minimal obstruction to aqueous humor flowing along the length of Schlemm's canal. Reinforcing Schlemm's canal with minimal metal mass present in the canal may also encourage a safe healing response over time.

Some exemplary ocular implants disclosed in this document comprise a body defining openings that are sized and shaped to facilitate the lateral flow of aqueous humor across and/or through the body of the ocular implant. The lateral flow of aqueous humor may include the flow of aqueous humor through the trabecular mesh and into Schlemm's canal. The lateral flow of aqueous humor may also include the flow of aqueous humor through outlets that communicate with Schlemm's canal.

One aspect of the invention provides an ocular implant adapted to reside at least partially in a portion of Schlemm's canal of an eye. In some embodiments, the ocular implant has a body extending in a curved volume whose longitudinal axis forms an arc of a circle, and a plurality of open areas and strut areas formed in the body, the open areas extending over more than 50% of a surface defining the curved volume, the strut areas surrounding the open areas, the body having a diameter of between 0.005 inches and 0.04 inches.

In some embodiments, the open areas are formed in a first longitudinal section extending along the curved volume. This longitudinal section may include the largest radius portion of the curved volume. The open areas of the implant may also include a plurality of openings formed on a second longitudinal section of the implant body disposed, e.g., opposite the first longitudinal section. In addition, there may be spine sections disposed between the openings formed on the second longitudinal section.

In some embodiments, the strut areas extend axially and circumferentially around the body from one side of the first longitudinal section to the other side of the first longitudinal section. Some of the open areas may be formed between the strut areas.

In some embodiments, the implant is formed from shape memory material in a shape approximately equal to the curved volume. The curved volume of the implant may extend through a 60°-180° arc of a circle. In some embodiments, material coverage within the curved volume in circular cross-sections perpendicular to the longitudinal axis is less than 50% over greater than 90% of the implant.

In some embodiments, the implant has an inlet portion disposed at one end of the body in fluid communication with the body and extending inward from the circle arc. The inlet portion may extend at a 90° angle from a tangent drawn from a connection point of the inlet portion to the body. In some embodiments, the inlet portion has a length greater than the diameter of the body. The inlet portion may be formed, e.g., as a coil, a channel with at least one open longitudinal section, etc. in fluid communication with the body of the implant. The inlet portion may also extend along the same circle arc as the body.

In some embodiments, the implant may have a blunt tip disposed at one end, and there may be a lumen formed through the blunt tip.

In some embodiments, a therapeutic agent may be deposited on the body of the implant. The therapeutic agent may be an anti-glaucoma drug such as a prostaglandin analog (e.g., latanoprost).

Another aspect of the invention provides a method of treating glaucoma including the following steps: supporting tissue forming Schlemm's canal in an eye with an implant extending at least partially in the canal along an axial length within the canal; and contacting with the implant less than 50% of the tissue forming the canal along the axial length. In some embodiments, the implant has open areas separated by spine areas along a first longitudinal section, in which case the supporting step includes the step of orienting the first longitudinal section openings toward a trabecular mesh portion of the canal. The supporting step may also include the step of orienting a second longitudinal section of the implant which is at least 90% open opposite to the first longitudinal section within the canal.

In some embodiments, the supporting step includes the step of supporting with the implant tissue extending approximately 60°-180° around the canal.

In some embodiments, the method includes the step of providing fluid communication between an anterior chamber and the canal through the implant, such as by engaging trabecular mesh tissue with the implant.

In some embodiments, the supporting step includes the step of supporting the tissue with the implant such that material coverage of tissue by the implant in cross-sections of the implant perpendicular to a longitudinal axis of the canal is less than 50% over greater than 90% of the axial length of the implant.

In some patients, Schlemm's canal may have become compartmentalized. When this is the case, Schlemm's canal becomes a series of small compartments separated by discontinuities or partitions. As the ocular implant is advanced into Schlemm's canal, the distal tip of the ocular implant penetrates the discontinuities/partitions. This penetrating action re-establishes fluid communication between adjacent compartments. The body of the ocular implant facilitates flow across the partitions by remaining in Schlemm's canal after fluid communication has been re-established.

Some exemplary ocular implants disclosed herein include a blunt tip having a generally rounded shape. For example, the blunt tip may have a generally hemispherical shape. The generally rounded shape of the blunt tip may increase the likelihood that the body of the ocular implant will track Schlemm's canal as the ocular implant is advanced into the canal during an implant procedure.

Some exemplary ocular implants disclosed in this document include an inlet portion that is shaped and sized to extend through the trabecular meshwork of the eye. This inlet portion may provide a flow path between the anterior chamber and Schlemm's canal. After entering Schlemm's canal, aqueous humor may flow between a proximal portion of the ocular implant and an intermediate portion of the ocular implant. The intermediate portion of the ocular implant may be conceptualized as a manifold that distributes the aqueous humor along a portion of Schlemm's canal. A plurality of outlets may be located along the length of this portion of Schlemm's canal. When this is the case, the presence of the ocular implant in Schlemm's canal facilitates the flow of aqueous humor through those outlets.

BRIEF DESCRIPTION OF THE DRAWINGS

FIGS. 7A, 7B, and 7C are side, bottom and top plan views (respectively) illustrating an exemplary ocular implant.

FIGS. 13A, 13B, and 13C are side, bottom and top plan views (respectively) illustrating another exemplary ocular implant.

DETAILED DESCRIPTION OF THE PREFERRED EMBODIMENT

The following detailed description should be read with reference to the drawings, in which like elements in different drawings are numbered identically. The drawings, which are not necessarily to scale, depict exemplary embodiments and are not intended to limit the scope of the invention. Examples of constructions, materials, dimensions, and manufacturing processes are provided for selected elements. All other elements employ that which is known to those of skill in the field of the invention. Those skilled in the art will recognize that many of the examples provided have suitable alternatives that can be utilized.

Figure 1:
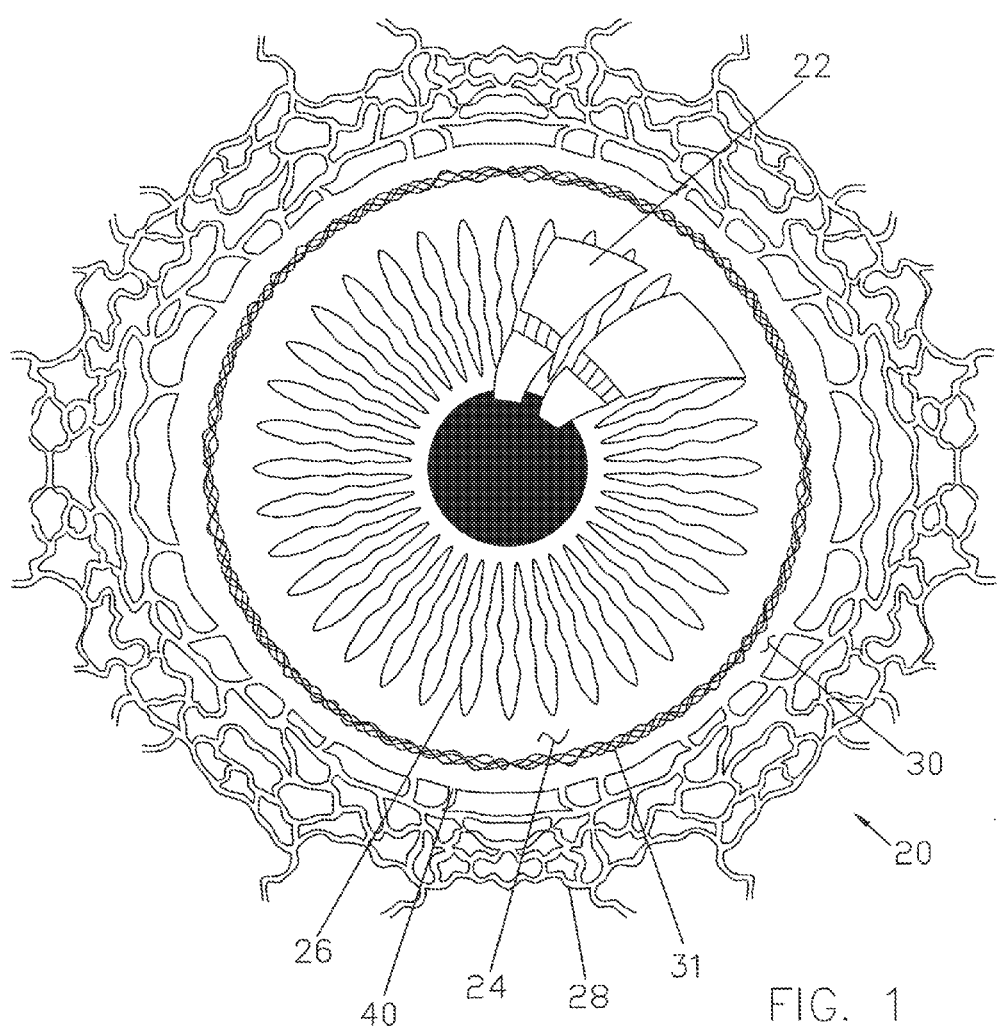
FIG. 1 is a plan view showing a portion of an eye.

FIG. 1 is a plan view showing a portion of an eye 20. A reflection on the outer surface of the cornea 22 of eye 20 is visible in FIG. 1. Cornea 22 encloses an anterior chamber 24 of eye 20. The iris 26 of eye 20 is visible through cornea 22 and anterior chamber 24. Anterior chamber 24 is filled with aqueous humor which helps maintain the generally hemispherical shape of cornea 22.

Whenever a person views an object, he or she is viewing that object through the cornea, the aqueous humor, and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the eye as new aqueous humor is secreted by the epithelial cells of the ciliary body. This excess aqueous humor enters the blood stream and is carried away by venous blood leaving the eye. The structures that drain aqueous humor from anterior chamber 24 include Schlemm's canal 30 and a large number of veins 28.

In FIG. 1, Schlemm's canal 30 can be seen encircling iris 26. Aqueous humor exits anterior chamber 24 and enters Schlemm's canal 30 by flowing through a trabecular mesh 32. Aqueous humor exits Schlemm's canal 30 by flowing through a number of outlets 40. After leaving Schlemm's canal 30, aqueous humor travels through veins 28 and is absorbed into the blood stream. Schlemm's canal typically has a non-circular cross-sectional shape whose diameter can vary along the canal's length and according to the angle at which the diameter is measured. In addition, there may be multiple partial pockets or partial compartments (not shown in these figures) formed along the length of Schlemm's canal. The shape and diameter of portions of Schlemm's canal and the existence and relative location of partial pockets or compartments may limit or prevent fluid flow from one point of Schlemm's canal to another. Hence, each outlet 40 from Schlemm's canal may drain only a portion of Schlemm's canal.

Figure 2:
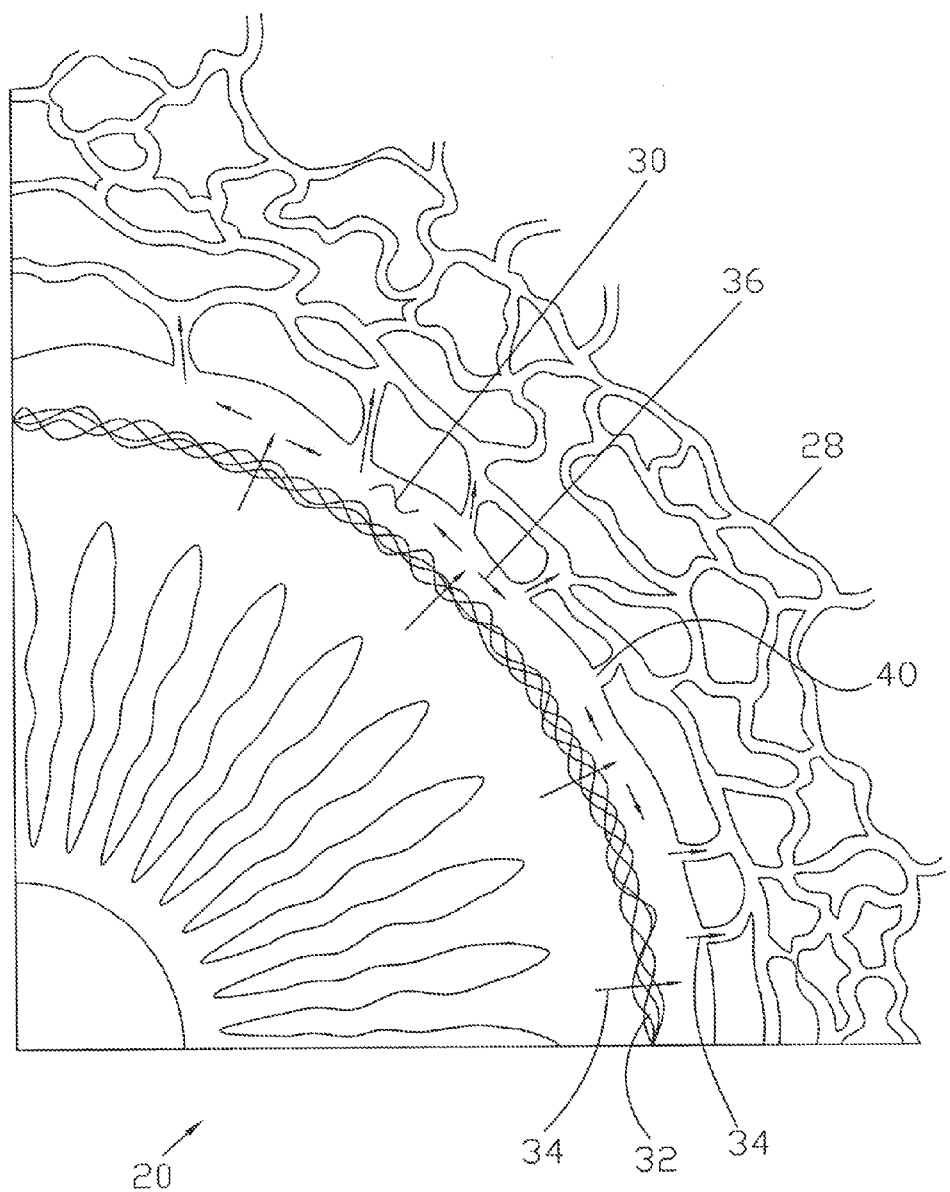
FIG. 2 is an enlarged plan view of a portion of the eye shown in the previous figure.

FIG. 2 is an enlarged plan view of a portion of eye 20 shown in the previous figure. The flow of aqueous humor in eye 20 is illustrated using arrows in FIG. 2. In FIG. 2, aqueous humor flowing through trabecular mesh 32 and into Schlemm's canal 30 is represented by a number of lateral flow arrows 34. The flow of aqueous humor along the length of Schlemm's canal is illustrated using a number of axial flow arrows 36.

With reference to FIG. 2, it will be appreciated that a number of outlets 40 communicate with Schlemm's canal 30. In FIG. 2, the flow of aqueous humor exiting Schlemm's canal 30 and flowing through outlets 40 is illustrated with additional lateral flow arrows 34. After leaving Schlemm's canal 30, aqueous humor travels through veins 28 and is absorbed into the blood stream.

Figure 3:
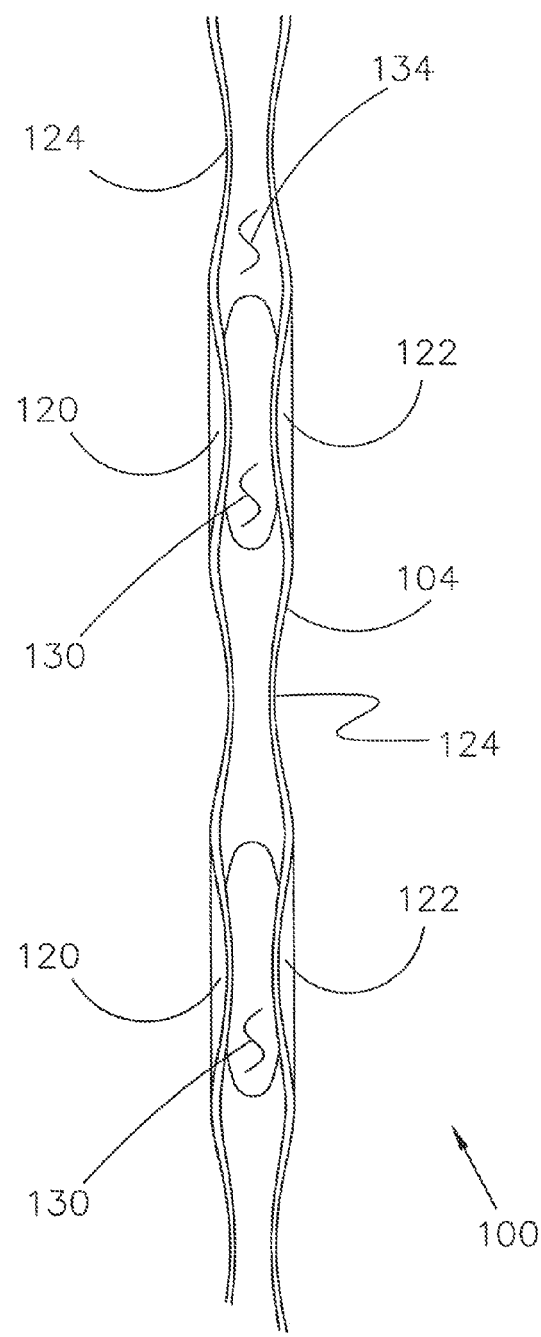
FIG. 3 is a top plan view showing an intermediate portion of an exemplary ocular implant.
Figure 4:
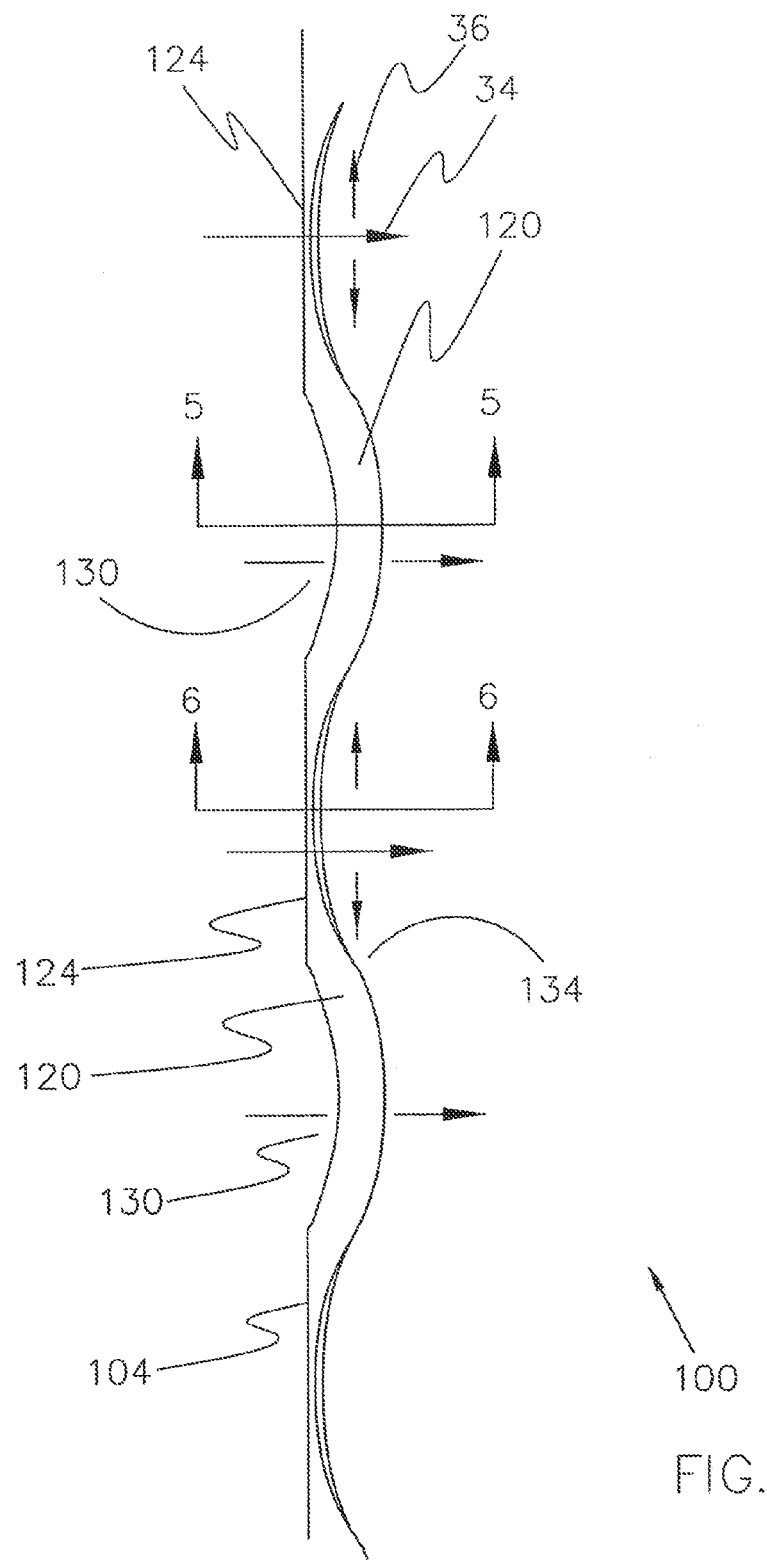
FIG. 4 is a sideplan view of the ocular implant shown in the previous figure.

FIGS. 3 and 4 are top and side views showing an intermediate portion of an exemplary ocular implant 100. Ocular implant 100 may be inserted into Schlemm's canal, the trabecular meshwork and the anterior chamber to facilitate the outflow of aqueous humor from the anterior chamber. This flow may include axial flow along Schlemm's canal, flow from the anterior chamber into Schlemm's canal, and flow leaving Schlemm's canal via outlets communicating with Schlemm's canal. When in place within the eye, ocular implant 100 will support trabecular mesh tissue and Schlemm's canal tissue and will provide for improved communication between the anterior chamber and Schlemm's canal (via the trabecular meshwork) and between pockets or compartments along Schlemm's canal.

Ocular implant 100 of FIGS. 3 and 4 comprises a body 104 having an outer surface 106. Body 104 of ocular implant 100 has a plurality of pairs of struts 120 and 122 separated by spine sections 124. The struts and spines define an open channel 134 whose open side lies along one longitudinal section of the implant body. A plurality of openings 130 are formed between the struts 120 and 122 on a longitudinal section of the implant opposite to the open side of channel 134. While in this embodiment the openings 130 are 180° from the open side of channel 134, in other embodiments openings 130 may be disposed 140°-150° the open side of channel 134. The diameter of body 104 is selected to support the tissue of Schlemm's canal without stretching it and is preferably in the range of 0.005 inches to 0.04 inches, most preferably in the range of 0.005 inches to 0.02 inches.

As shown in these figures, aqueous humor may flow axially down open channel 134 (as shown by arrows 36 in FIG. 4) or out of the implant through the opening of open channel 134 (first passing, e.g., through openings 130 and/or along the channel 134) as represented by lateral flow arrows 34. When implanted, body 104 of implant 100 preferably extends 60°, 90°, 150° or 180° around the circle formed by Schlemm's canal. The arrangement of struts, open areas and spine areas along implant 100 supports the tissue of Schlemm's canal with a minimum amount of material. In the embodiment shown in FIGS. 3 and 4, for example, the open areas extend over more than 50% of a hypothetical surface covering the volume of the portion of the implant lying within Schlemm's canal. This combination of features helps aqueous humor flow between any pockets or compartments formed within Schlemm's canal and, therefore, between the anterior chamber and the outlets from Schlemm's canal to the venous system.

Figure 5:
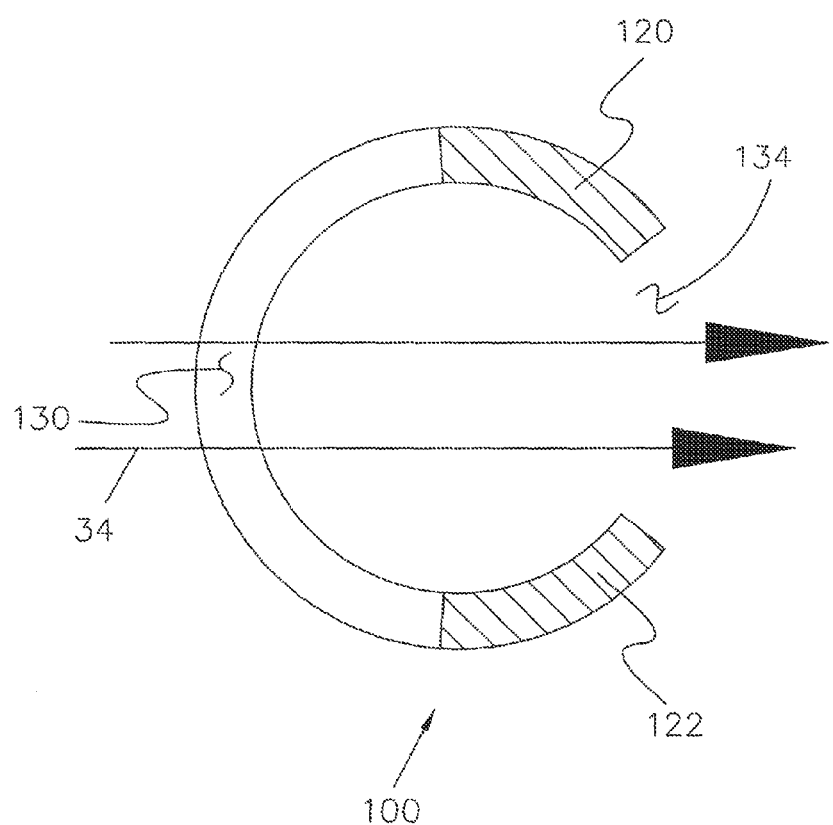
FIG. 5 is a lateral cross-sectional view of the ocular implant shown the previous figure.
Figure 6:
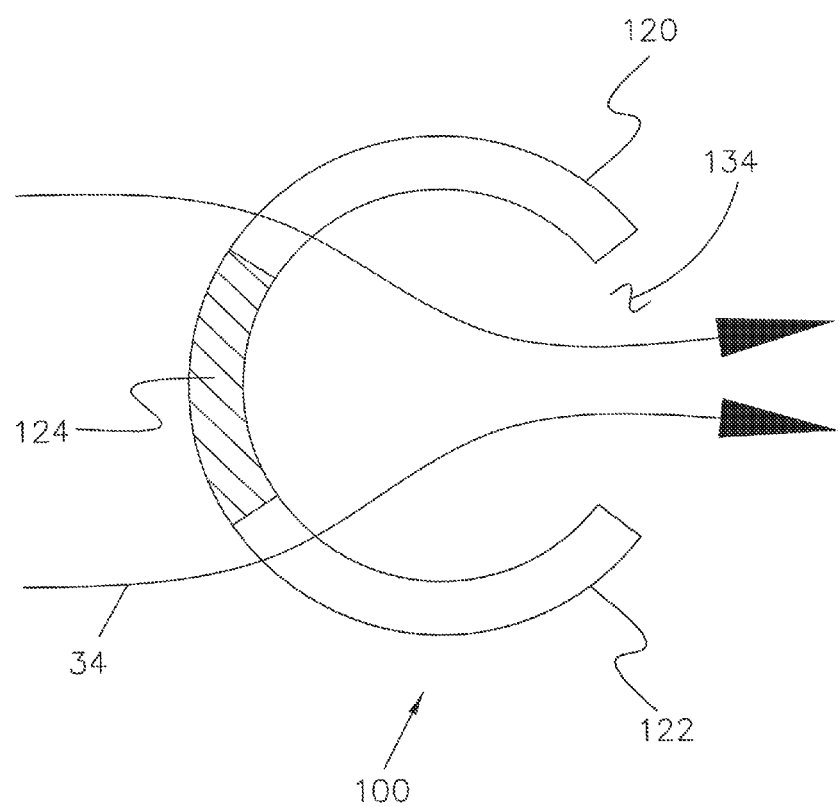
FIG. 6 is an additional lateral cross-sectional view of the ocular implant shown the previous figure.

FIG. 5 is a lateral cross-sectional view of ocular implant 100 taken along line 5-5 shown in FIG. 4, and FIG. 6 is a lateral cross-sectional view of ocular implant 100 taken along line 6-6 shown in FIG. 4. There are normally many flow paths from the anterior chamber through the trabecular meshwork into Schlemm's canal. Aqueous humor may therefore flow into channel 134 in body portion 104 of implant 100 from the trabecular meshwork through one or more openings 130 and/or around the struts 120/122 and spines 124. Thus, in FIG. 5, aqueous humor flowing past a spine area 124 is illustrated with lateral flow arrows 34, and in FIG. 6, aqueous humor flowing between first strut area 120 and second strut area 122 is illustrated using lateral flow arrows 34.

FIGS. 5 and 6 also illustrate another unique feature of implant 100: The arrangement of struts, openings and spine areas ensures that material coverage of Schlemm's canal in virtually any cross-section of the implant and canal is less than 50%. This material coverage relationship hold true for over 90% of the implant's length.

Figure 8B:
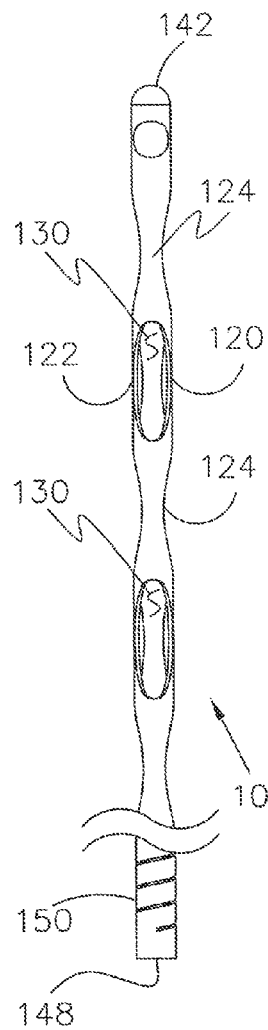
FIGS. 8A, 8B, and 8C are additional, larger side, bottom and top plan views (respectively) of the exemplary ocular implant shown in FIGS. 7A, 7B, and 7C.
Figure 8A:
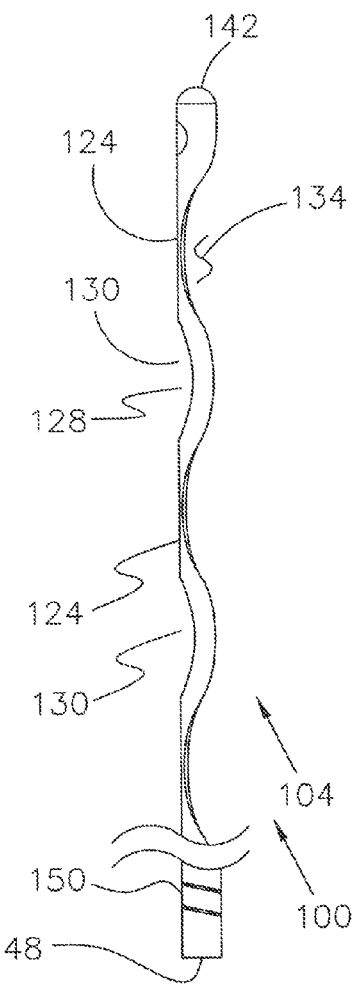
Figure 8C:
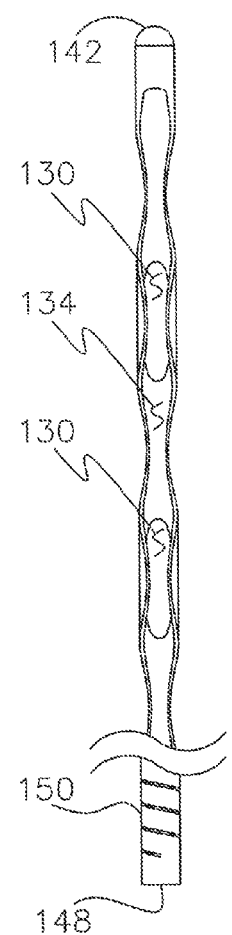

In some embodiments, in addition to a Schlemm's canal portion as described above, the ocular implant also includes at least one optional inlet portion adapted to be disposed in the anterior chamber of the eye. The inlet portion is configured to support trabecular mesh tissue and to permit aqueous humor to flow from the anterior chamber into the open channel of the implant within Schlemm's canal. FIGS. 7A-C and 8A-C illustrate an exemplary ocular implant 100 with an optional inlet region 150 in addition to a plurality of struts 120, 122, openings 130 and spine areas 124 substantially the same as the previous embodiment. In the embodiment of FIGS. 7 and 8, inlet region 150 of ocular implant 100 comprises a coil. Coil 150 comprises a plurality of turns 152 that are defined by a generally helical slot 154. Coil 150 may be bent so as to project through the trabecular mesh into the anterior chamber while the remainder of the device lies within Schlemm's canal. Aqueous humor can flow into the inlet region through an open end 148 and through slot 154.

In some embodiments, the ocular implant may have an optional blunt tip for use in facilitating atraumatic delivery of the device into Schlemm's canal. As shown in FIGS. 7 and 8, distal portion 140 of ocular implant 100 comprises a blunt tip 142. In some useful embodiments of ocular implant 100, blunt tip 142 has a generally rounded shape. In the embodiment shown in FIGS. 7 and 8, blunt tip 142 has a generally hemispherical shape.

In the embodiment of FIGS. 7 and 8, body 104 of ocular implant 100 is pictured assuming a generally straight shape. Embodiments of ocular implant 100 are possible in which body 104 has a generally curved resting shape.

Ocular implant 100 can be fabricated, for example, by providing a tube and laser cutting openings in the tube to form the shape shown in FIGS. 7 and 8. Body 104 of ocular implant 100 can be fabricated from various biocompatible material possessing the necessary structural and mechanical attributes. Both metallic and non-metallic materials may be suitable. Examples of metallic materials include stainless steel, tantalum, gold, titanium, and nickel-titanium alloys known in the art as Nitinol. Nitinol is commercially available from Memry Technologies (Brookfield, Conn.), TiNi Alloy Company (San Leandro, Calif.), and Shape Memory Applications (Sunnyvale, Calif.).

Ocular implant 100 may include a therapeutic agent deposited on body 104. The therapeutic agent may, for example, be incorporated into a polymeric coating that is deposited out the outer surface 106 of body 104. The therapeutic agent may comprise an anti-glaucoma drug. Examples of anti-glaucoma drugs include prostaglandin analogs. Examples of prostaglandin analogs include latanoprost.

Ocular implant 100 may be used in conjunction with a method of treating a patient. Some such methods may include the step of inserting a core member into a lumen defined by ocular implant 100. The core member may comprise, for example, a wire or tube. The distal end of the ocular implant may be inserted into Schlemm's canal. The ocular implant and the core member may then be advanced into Schlemm's canal until the ocular implant has reached a desired position. The core member may then be withdrawn from the ocular implant.

Figure 9:
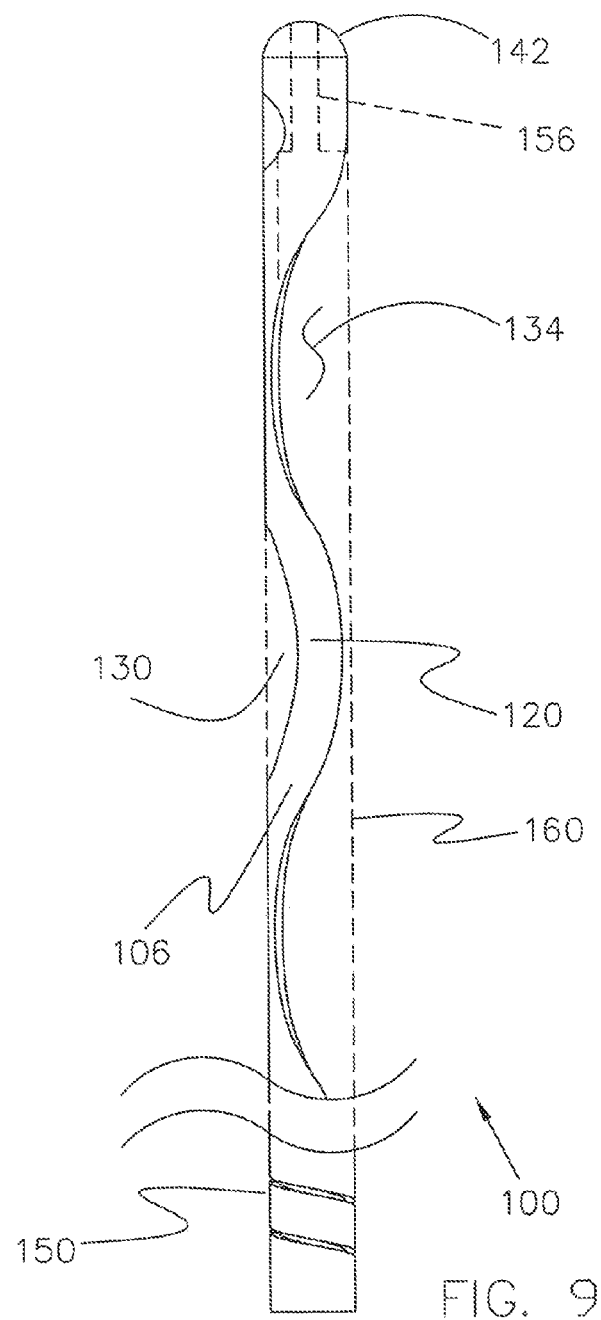
FIG. 9 is an additional side plan view illustrating the ocular implant shown in the previous figure.
Figure 10:
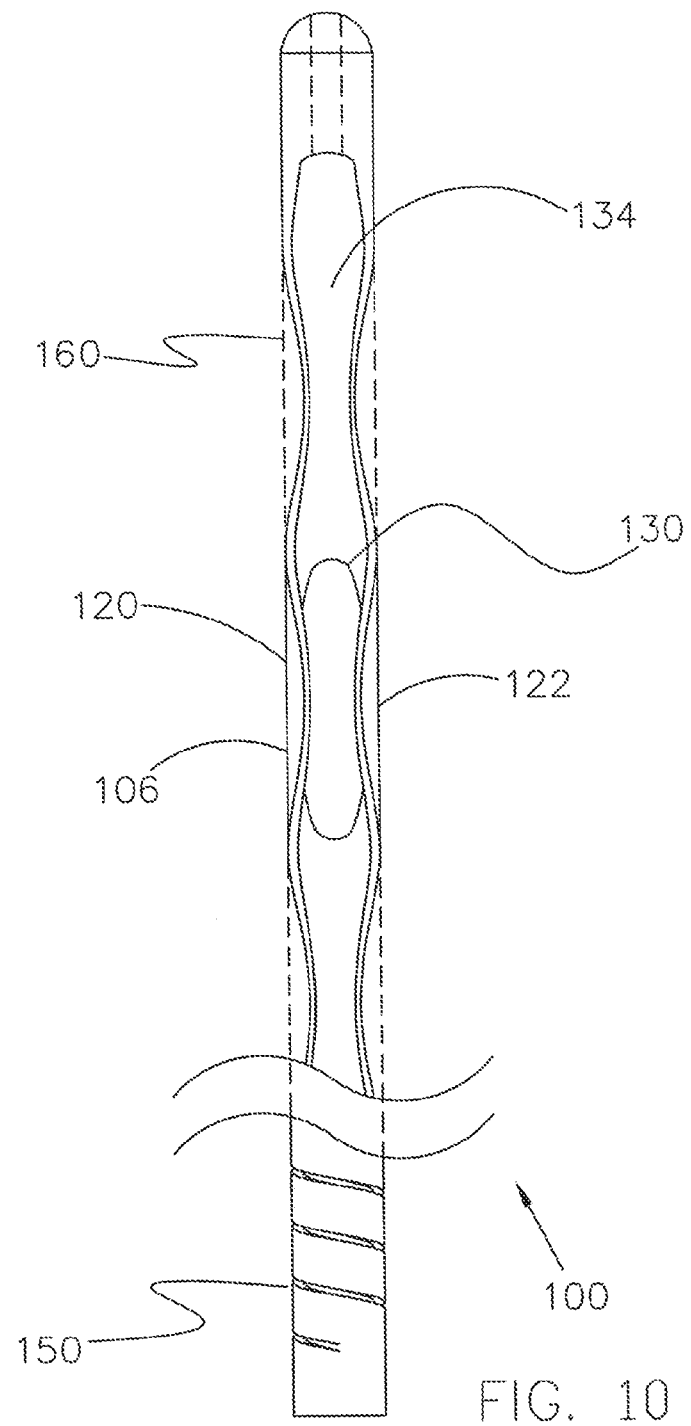
FIG. 10 is a top plan view illustrating the ocular implant shown in the previous figure.

FIGS. 9 and 10 show another embodiment of an ocular implant 100 similar to that of FIGS. 7 and 8. With reference to FIGS. 9 and 10, a lumen 156 is formed in blunt tip 142. This lumen may be used to inject a contrast medium through the blunt tip during implantation of the implant into the patient's eye. Lumen 156 may also be used to inject a visco-elastic medium in front of the implant to part tissue as the implant moves into Schlemm's canal.

A dotted line 160 in FIGS. 9 and 10 indicates a cylindrical envelope surrounding implant 100. In some embodiments, the open areas of ocular implant 100 (made up of openings 130 and the open portion of open channel 134) extend over more than 50% of cylindrical surface 160.

Figure 11:
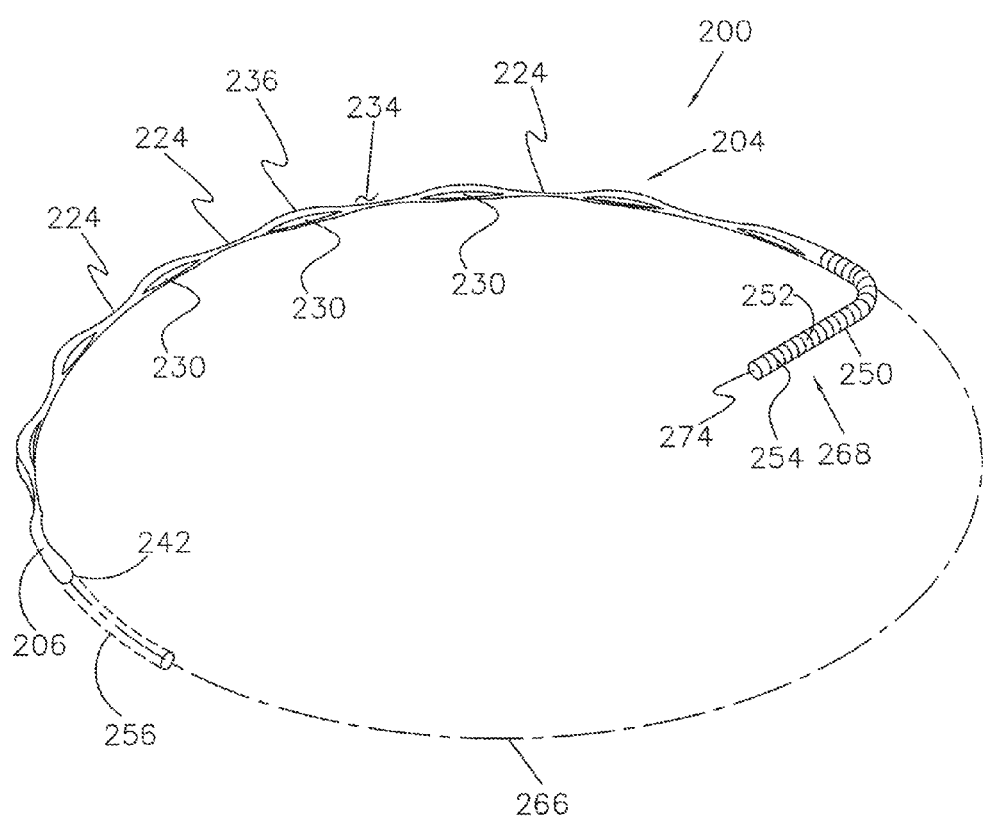
FIG. 11 is a perspective view of an exemplary ocular implant.
Figure 12:
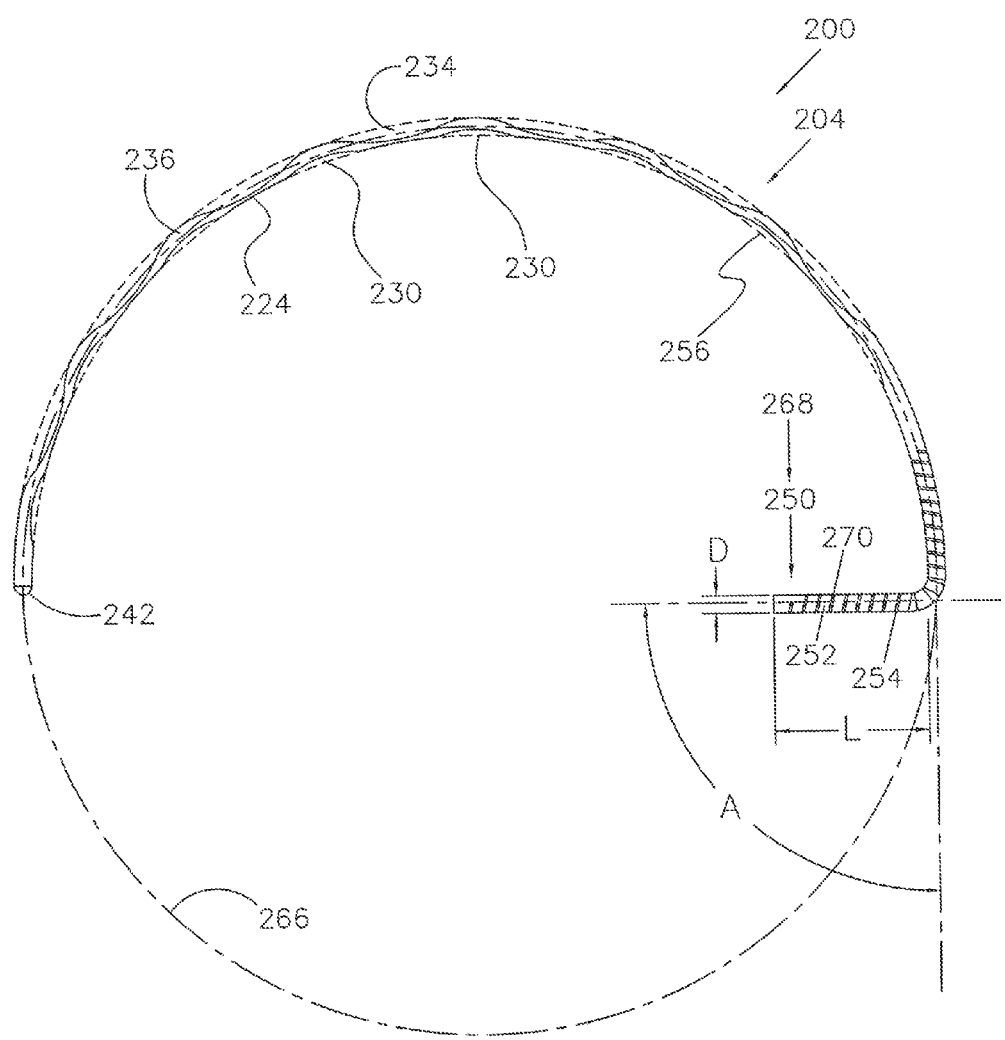
FIG. 12 is a plan view of an additional exemplary ocular implant.

FIGS. 11 and 12 show an additional exemplary ocular implant 200 according to the invention. In the embodiment of FIGS. 11 and 12, no external forces are acting on ocular implant 200, and ocular implant 200 is free to assume a generally curved resting shape in which its longitudinal axis forms an arc of a circle 266, as depicted in FIGS. 11 and 12. In some useful embodiments of ocular implant 200, a relatively stiff core may be placed in the ocular implant 200 to cause it to assume a generally straight shape during delivery.

As shown in FIGS. 11 and 12, implant 200 has a plurality of openings 230 along a longitudinal section on a shorter radius side of the body, as well as an open channel 234 facing radially outward on a longitudinal section forming the largest radius portion of the body. As in the prior embodiments, implant 200 also has a plurality of struts 236 and spine areas 224 formed in the body portion 204 of the implant. As shown, the open areas (including the openings 230 and the open portion of channel 234) extend over more than 50% of the surface of a hypothetical cylinder 256 surrounding the implant 200. In addition, material coverage of Schlemm's canal in cross-sections taken over 90% of the length of implant 200 is less than 50%, as in the previous embodiment.

Ocular implant 200 of FIGS. 11 and 12 includes an inlet portion 268 extending inward from circle 266. Inlet portion 268 of ocular implant 200 comprises a coil 250 having a plurality of turns 252 that are defined by a generally helical slot 254. An inlet 274 is formed in one end of inlet portion 268. Inlet portion 268 will extend through the trabecular meshwork into the anterior chamber of the eye when body portion 204 lies in Schlemm's canal.

Ocular implant 200 of FIGS. 11 and 12 includes a blunt tip 242 with a generally rounded shape. The generally rounded shape of blunt tip 242 may increase the likelihood that body 204 will track Schlemm's canal as ocular implant 200 is advanced into the canal during an implant procedure.

As shown in FIGS. 11 and 12, ocular implant 200 extends through a 180° arc of circle 366. Other implant sizes are possible, of course, such as implants extending 60°, 90° and 150° around a circle. As shown in FIG. 12, inlet portion 268 is shown extending at an angle A from a tangent line T. In the embodiment of FIG. 13, angle A is about 90 degrees. Inlet portion 268 has a length L and body 204 of ocular implant 300 has a diameter D. In the embodiment of FIG. 12, length L is greater than diameter D. As in the other embodiments, the diameter can range from 0.005 inches to 0.04 inches, preferably from 0.005 inches to 0.02 inches, in order to lie within and support Schlemm's canal.

Figure 18:
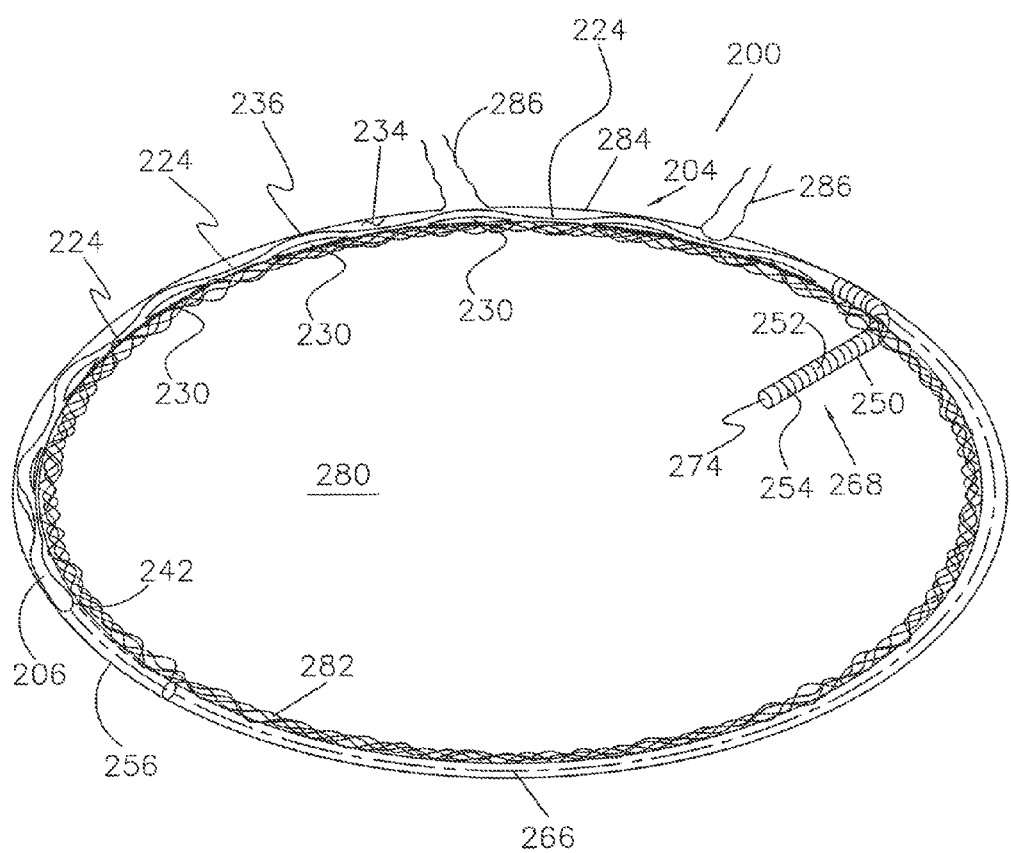
FIG. 18 shows the ocular implant of FIGS. 11 and 12 in place within a patient's eye.

FIG. 18 shows the implant of FIGS. 11 and 12 in place within a patient's eye. The body portion (including the plurality of strut pairs 236, openings 230, open channel 234, spine areas 224 and the blunt tip 242) lie within and support the walls of Schlemm's canal 284. The openings 230 are oriented at least partially toward the trabecular meshwork 282, and the open portion of open channel 234 is oriented on the largest radius portion of the canal facing openings 286 from Schlemm's canal into the venous system (not shown). As shown, the body of the implant extends approximately 180° around the canal. The inlet portion 250 of the implant extends through the trabecular meshwork 282 into the anterior chamber 280 so that the inlet 274 and spiral slot 254 are in fluid communication with the aqueous humor within the anterior chamber.

FIGS. 13A-C show an additional exemplary ocular implant 400. As in the embodiments shown above, ocular implant 400 comprises a body 404 having a plurality of openings 430, an open channel 434, pairs of struts 420 and 422, and spine areas 424. As in the earlier embodiments, the open areas (including the openings 430 and the open portion of channel 434) extend over more than 50% of a hypothetical cylinder surrounding the body portion 404 of implant 400, and material coverage of Schlemm's canal in cross-sections taken over 90% of the length of the implant 400 is less than 50%. A blunt tip 442 is also provided, as in the earlier embodiments.

The inlet portion 450 of the implant differs from prior embodiments, however. Inlet portion 450 is formed as an open channel 476. When the body portion 404 of the implant is disposed in Schlemm's canal and inlet portion 450 projects through the trabecular meshwork into the anterior chamber, aqueous humor can flow into the implant through the open channel 476 and then into the body portion 404 within Schlemm's canal. The open nature of inlet portion 450 reduces the speed with which aqueous humor will flow into the implant, thereby reducing potential damage to adjacent tissue from suction forces associated with the flow.

Figure 14:
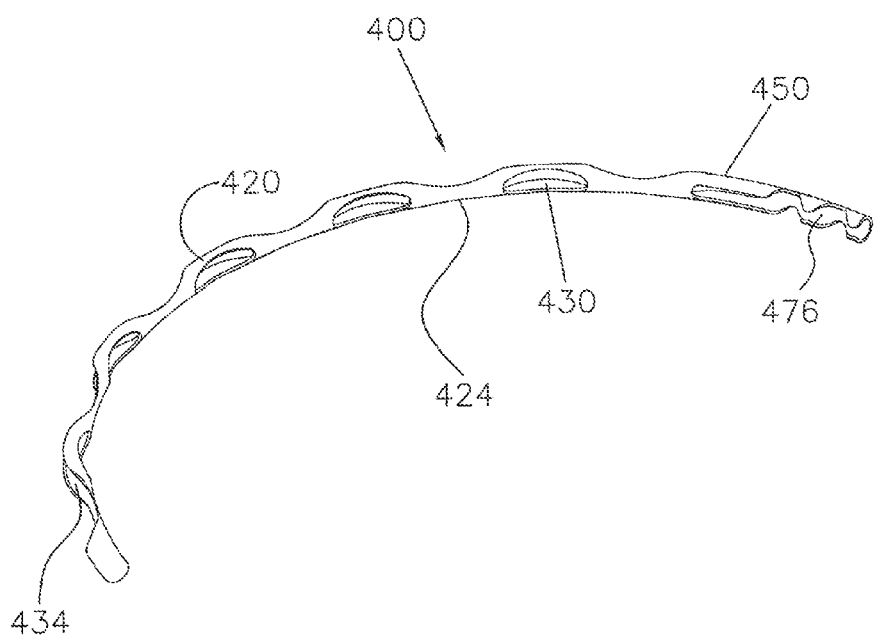
FIG. 14 is a perspective view of an ocular implant.
Figure 15:
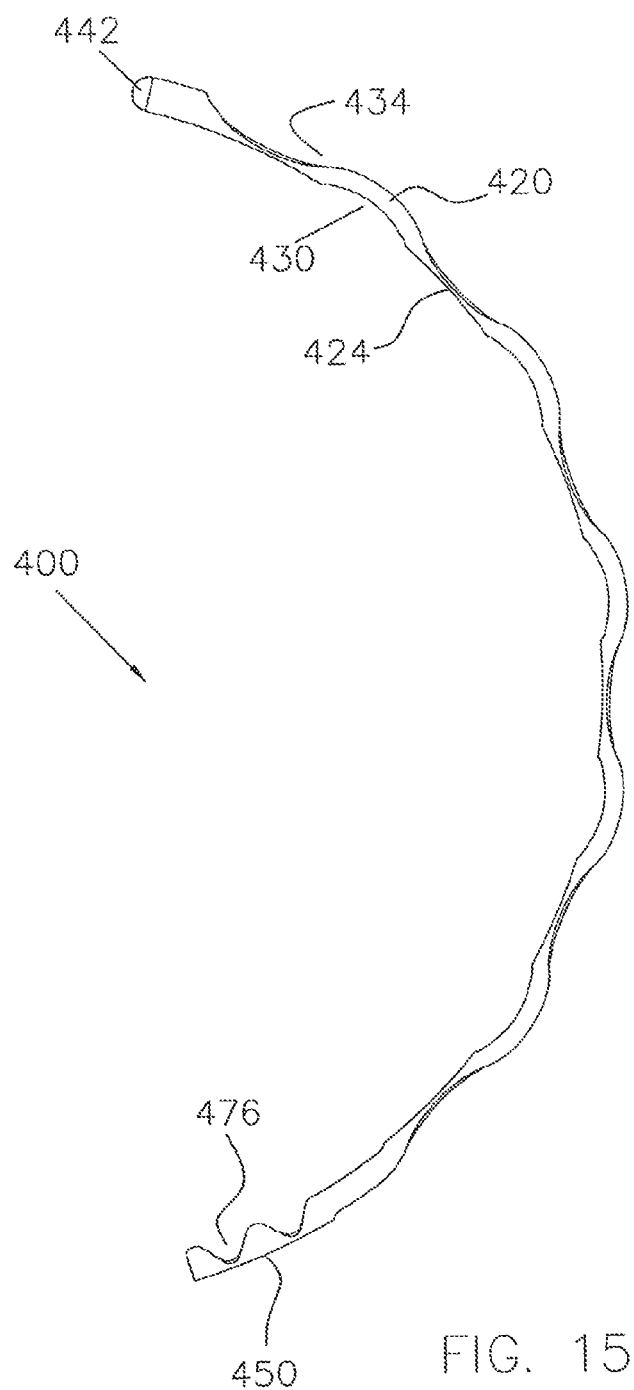
FIG. 15 is a side view of the ocular implant of FIG. 14.
Figure 16:
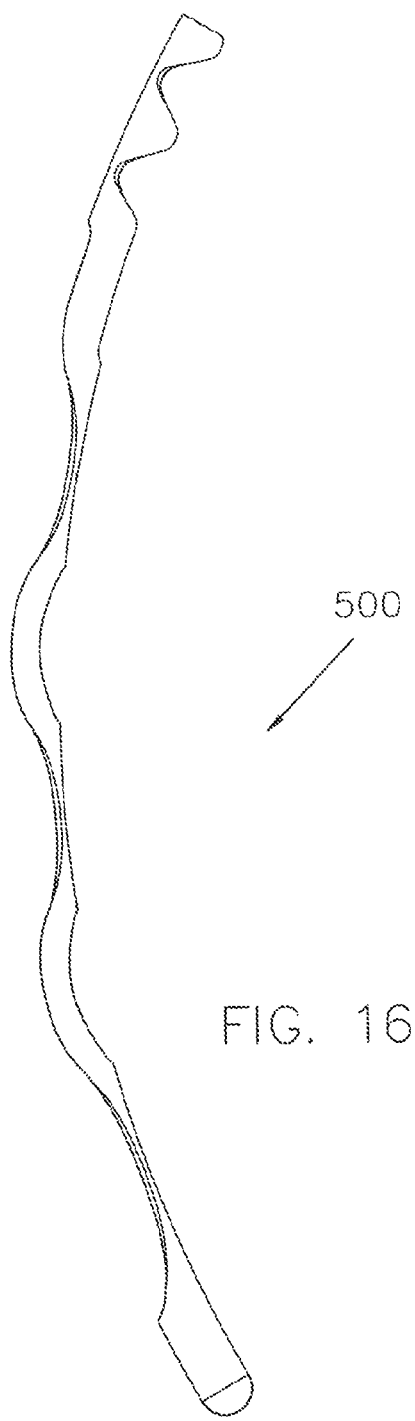
FIG. 16 is a perspective view of yet another ocular implant.
Figure 17:
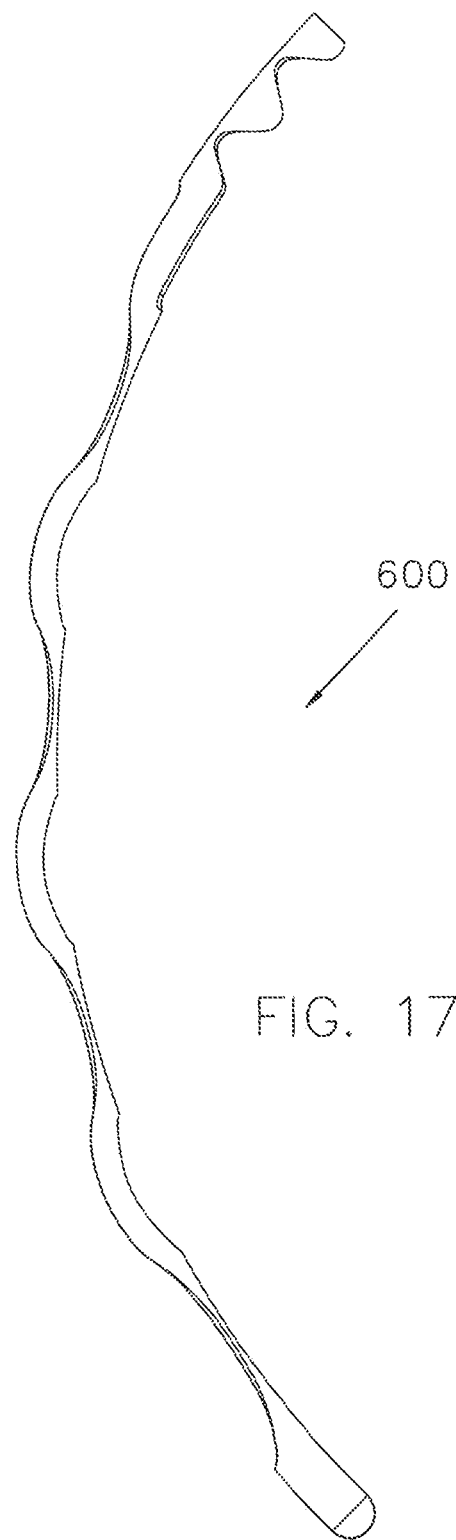
FIG. 17 is a perspective view of still another ocular implant.

FIGS. 14 and 15 show embodiments similar to that of FIG. 13 in which the implant 400 has an at rest shape in the form of an arc of a circle. As in the earlier embodiments, the implant may extend around any portion of the circle, such as 60°, 90°, 150° or 180°. For example, the implant of FIGS. 14 and 15 extends in a 150° arc, an implant 500 extending in a 60° arc is shown in FIG. 16, and an implant 600 extending in a 90° arc is shown in FIG. 17.

Unlike the embodiment shown in FIGS. 11 and 12, however, inlet portion 450 lies along the same circle arc as the rest of the implant. When inlet portion 450 is disposed in the anterior chamber (as shown in FIG. 19) and the other portions of the implant lie in Schlemm's canal, the direction of axial flow of aqueous humor from inlet 450 into open channel 434 does not change as dramatically as in embodiments in which the inlet portion is at a 90° angle to the body portion of the implant.

Figure 19:
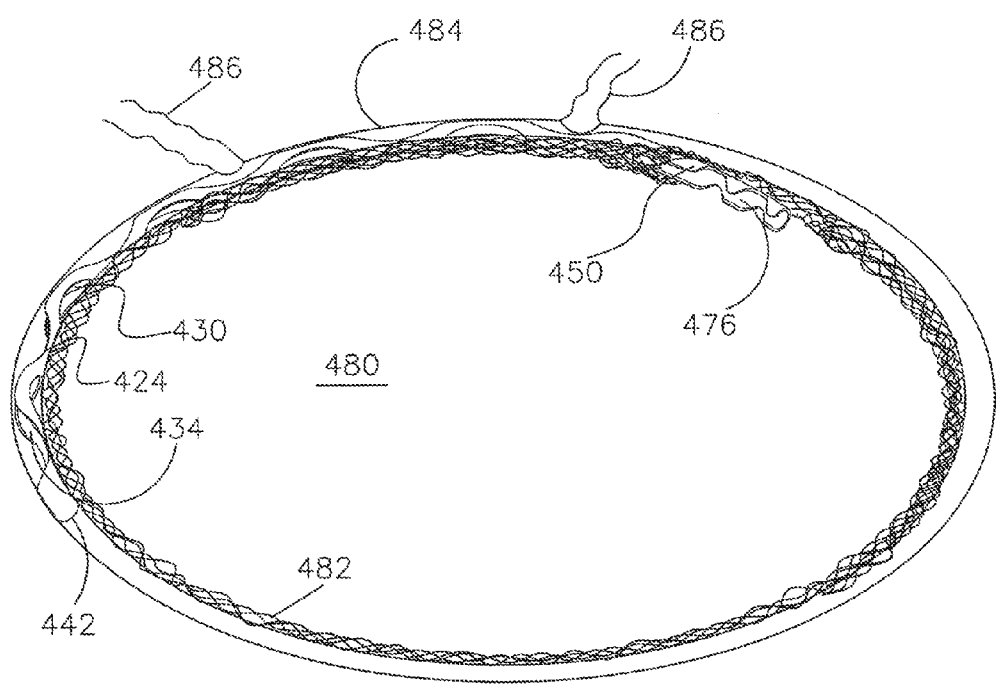
FIG. 19 shows the ocular implant of FIGS. 14 and 15 in place within a patient's eye.

FIG. 19 shows the implant of FIGS. 14 and 15 in place within a patient's eye. The body portion (including the plurality of strut pairs 420, openings 430, open channel 434, spine areas 424 and the blunt tip 442) lie within and support the walls of Schlemm's canal 484. The openings 430 are oriented at least partially toward the trabecular meshwork 482, and the open portion of open channel 434 is oriented on the largest radius portion of the canal facing openings 486 from Schlemm's canal into the venous system (not shown). As shown, the body of the implant extends approximately 150° around the canal. The inlet portion 450 of the implant extends through the trabecular meshwork 482 into the anterior chamber 480 so that the open channel 476 of the inlet portion is in fluid communication with the aqueous humor within the anterior chamber.

While exemplary embodiments of the present invention have been shown and described, modifications may be made, and it is therefore intended in the appended claims to cover all such changes and modifications which fall within the true spirit and scope of the invention.

What is claimed is:

1. A method of treating glaucoma comprising:
   inserting an ocular implant into a human eye, the ocular implant comprising an inlet portion at a proximal end, the inlet portion comprising an opening, a Schlemm's canal portion disposed distal to the inlet portion, the Schlemm's canal portion having an elongate opening extending longitudinally along the implant and a central channel extending through the inlet portion and the Schlemm's canal portion, the central channel being in fluid communication with the inlet opening and the elongate opening;
   advancing the Schlemm's canal portion of the implant into Schlemm's canal, so that the Schlemm's canal portion tracks Schlemm's canal as it is advanced;
   orienting the elongate opening toward collector channels in communication with Schlemm's canal; and
   disposing the inlet portion opening in an anterior chamber of the eye.

2. The method of claim 1 wherein the inlet portion opening comprises an open channel extending longitudinally along the inlet portion, the step of disposing the inlet portion comprising disposing the inlet portion in the anterior chamber so that the open channel faces away from the meshwork.

3. The method of claim 1 wherein the step of disposing the Schlemm's canal portion of the inlet in Schlemm's canal comprises extending the Schlemm's canal portion within Schlemm's canal 60°-180° around the pupil of the eye.

4. A method of treating glaucoma comprising:
   inserting an ocular implant into a human eye, the ocular implant comprising a central channel;
   disposing an inlet portion of the implant in an anterior chamber of the eye, the inlet portion comprising an opening in fluid communication with the central channel;
   disposing a Schlemm's canal portion of the inlet in Schlemm's canal, the Schlemm's canal portion having an elongate opening extending longitudinally along the implant in fluid communication with the central channel; and
   orienting the elongate opening toward collector channels in communication with Schlemm's canal;
   wherein the Schlemm's canal portion of the implant comprises a first spine extending longitudinally along the central channel, a second spine extending longitudinally along the central channel, the second spine being disposed distal to the first spine, a first frame extending longitudinally along the central channel, the first frame being disposed distal to the first spine and proximal to the second spine, the first frame having a circumferential extent around the central channel greater than a circumferential extent of the first spine and a circumferential extent of the second spine, and a second frame extending longitudinally along the central channel, the second frame being disposed distal to the second spine, the second frame having a circumferential extent around the central channel greater than the circumferential extent of the first spine and the circumferential extent of the second spine, the elongate opening extending longitudinally along a portion of a curved volume bordered by the spines and the frames the method further comprising orienting the spines away from the collector channels.

5. The method of claim 4 wherein the method further comprises orienting the spines against the meshwork.

6. The method of claim 4 wherein the first and second frames each comprise an opening circumferentially offset from the elongate opening and in fluid communication with the central channel, the method further comprising orienting the first and second frame openings against the meshwork.

7. The method of claim 1 wherein the ocular implant is curved and the inlet portion extends along the curve.

8. The method of claim 1 wherein the ocular implant is curved, the elongate opening facing radially outward from the implant.

9. The method of claim 8 wherein the ocular implant further comprises a plurality of openings on a smaller radius side of the Schlemm's canal portion of the implant than the elongate opening.

10. The method of claim 9 further comprising orienting the plurality of openings toward trabecular meshwork.

11. The method of claim 1 further comprising supporting the trabecular meshwork with the inlet portion.

12. The method of claim 1 wherein the elongate opening extends along all of the Schlemm's canal portion of the implant, the advancing step comprising advancing all of the Schlemm's canal portion of the implant into and along Schlemm's canal.

13. A method of treating glaucoma comprising:
   inserting a curved ocular implant into a human eye, the ocular implant comprising an inlet portion at a proximal end, wherein the ocular implant terminates with the inlet portion, the inlet portion comprising an opening, a Schlemm's canal portion disposed distal to the inlet portion, the Schlemm's canal portion having an elongate opening extending longitudinally along the implant facing radially outward and a central channel extending through the inlet portion and the Schlemm's canal portion, the central channel being in fluid communication with the inlet opening and the elongate opening;
   advancing the Schlemm's canal portion of the implant into Schlemm's canal;
   orienting the elongate opening toward collector channels in communication with Schlemm's canal;
   disposing the inlet portion opening in an anterior chamber of the eye; and
   supporting trabecular meshwork with the inlet portion.

14. The method of claim 13 wherein the inlet portion extends along the curve of the implant.

15. The method of claim 13 wherein the ocular implant further comprises a plurality of openings on a smaller radius side of the Schlemm's canal portion of the implant than the elongate opening, the method further comprising orienting the plurality of openings toward trabecular meshwork.

16. The method of claim 13 wherein the elongate opening extends along all of the Schlemm's canal portion of the implant, the advancing step comprising advancing all of the Schlemm's canal portion of the implant into and along Schlemm's canal.

17. The method of claim 13 wherein the inlet portion opening comprises an open channel extending longitudinally along the inlet portion, the step of disposing the inlet portion comprising disposing the inlet portion in the anterior chamber so that the open channel faces away from the meshwork.

18. The method of claim 13 wherein the step of disposing the Schlemm's canal portion of the inlet in Schlemm's canal comprises advancing the Schlemm's canal portion within Schlemm's canal 60°-180° around the pupil of the eye.

* * * * *